United States Patent [19]

Brodoway

[11] 4,102,801

[45] Jul. 25, 1978

[54] PROCESS FOR MAKING POLYAMINE CARBAMATES

[75] Inventor: Nicolas Brodoway, Claymont, Del.

[73] Assignee: E. I. Du Pont de Nemours and Company, Wilmington, Del.

[21] Appl. No.: 780,908

[22] Filed: Mar. 24, 1977

[51] Int. Cl.$^2$ .......................... C09K 3/00; C01B 21/12; B01J 31/02
[52] U.S. Cl. .................................... 252/182; 252/426; 252/428; 252/430; 260/501.11
[58] Field of Search ............... 252/426, 428, 430, 182; 260/482 B, 514 J, 501.11

[56] References Cited

U.S. PATENT DOCUMENTS

| | | | |
|---|---|---|---|
| 3,185,673 | 5/1965 | Kendall et al. | 260/79.5 |
| 3,344,175 | 9/1967 | Canfield | 260/514 |
| 4,025,444 | 5/1977 | Murphy et al. | 260/501.11 |

OTHER PUBLICATIONS

Journal of American Chemical society, vol. 73; pp. 1829–1831 (1951).

*Primary Examiner*—P. E. Konopka

[57] ABSTRACT

Solventless process of reacting polyamine having two primary amino groups adsorbed on a particulate carrier with carbon dioxide to obtain the free-flowing corresponding polyamine carbamate-carrier mixture.

13 Claims, No Drawings

PROCESS FOR MAKING POLYAMINE CARBAMATES

BACKGROUND OF THE INVENTION

This invention relates to a process for producing polyamine carbamates.

Polyamines have been used as vulcanizing agents for elastomers, especially fluoroelastomers. Unfortunately, low molecular weight polyamines exhibit a number of undesirable properties: they are liquid, they are odorous, and they are corrosive. However, conversion of the polyamines to carbamates alleviates these problems and, therefore, polyamine carbamates have been used extensively as curing agents for elastomers, especially fluorinated olefin polymers and acrylate polymers containing carboxylic acid or reactive chloride cure-sites. Procedures for vulcanizing these polymers with polyamine carbamates are well known in elastomer technology and described in, for example, U.S. Pat. Nos. 3,029,227; 3,088,938; and 3,888,472. Polyamine carbamates are particularly useful as vulcanizing agents because they are solid (being ionic) derivatives of the polyamines, they do not have the disadvantages mentioned above common to polyamines per se, and they dissociate at vulcanization temperatures, e.g., in excess of 100° C, into their components, thus making the polyamine available for vulcanization.

Heretofore, polyamine carbamates have been prepared by dissolving a polyamine in an organic solvent and adding carbon dioxide to the solution. This procedure has been used commercially for the production of polyamine carbamates, but it does have certain disadvantages. Specifically, the solvent and the precipitated polyamine carbamate must be separated and the carbamate dried before it is ready for use. This is an expensive and time-consuming procedure. The present invention is directed to a process that is free from the above-mentioned difficulties and the material, labor and energy costs using the process of this invention are less than that of the generally used abovedescribed commercial procedure.

SUMMARY OF THE INVENTION

The present invention is directed to a solventless process for preparing polyamine carbamates that are used as vulcanizing agents for elastomers. More particularly, the invention is directed to an improvement in the process for preparing a polyamine carbamate which comprises reacting an aliphatic or cycloaliphatic polyamine having 2-14 carbon atoms and two primary amino groups with gaseous carbon dioxide, the improvement comprising mixing said polyamine and a particulate carrier capable of adsorbing the polyamine and reacting the polyamine on the carrier with carbon dioxide in the absence of solvent for the reactants to obtain the free-flowing, corresponding polyamine carbamate-carrier mixture. The carrier can be any suitable particulate material that is capable of adsorbing the polyamine. Preferably, the particulate carrier is a polyamine carbamate that has the same chemical composition as the carbamate being produced or an inert inorganic material.

PREFERRED EMBODIMENTS OF THE INVENTION

The carrier used in the present invention for the preparation of polyamine carbamates must have the capacity to adsorb the polyamine. Suitable carriers are particulate inorganic materials that are inert to the reaction of the polyamine with carbon dioxide, and polyamine carbamates in particulate form. Representative particulate inert inorganic carriers that can be used in the invention include silica, magnesium carbonate, magnesium oxide, aluminum hydrates, calcium and magnesium silicates (diatomaceous earths), carbon blacks, and aluminum silicates (clays). Quite conveniently, the carrier can be a polyamine carbamate in particulate form that is identical chemically to the polyamine carbamate that is being produced. For example, if 1,2-diaminopropane carbamate is being synthesized, the same carbamate can be used as the carrier. The carrier must be in particulate form and usually the diameter of the particles is about 0.1–40 microns, thus the particle size of the carrier is such that it will pass through a 325 mesh screen. When the particle size of the carrier is within the ranges mentioned above, the polyamine carbamate-carrier mixture can be used directly for the vulcanization of most elastomers and, generally, there is no need to micronize the carrier-carbamate mixture to reduce its particle size.

The polyamine that is adsorbed on the carrier is an aliphatic or cycloaliphatic polyamine that contains 2–14 carbon atoms and two primary amino groups. Such polyamines are readily available and they form effective curing agents when converted to the carbamate. Representative aliphatic and cycloaliphatic polyamines having 2–14 carbon atoms and two primary amino groups that can be used in the process of this invention for conversion to the corresponding polyamine carbamate include aliphatic and cycloaliphatic polyamines such as 1,2-diaminopropane, 1,6-diaminohexane, 1,2-diaminoethane, triethylenetetraamine, diethylenetriamine, 1,4-diaminobutane, 1,5-diaminopentane, 1,10-diaminodecane, 1,12-diaminododecane, 1,4-diaminocyclohexane and 4,4'-methylenebis(cyclohexylamine); $C_1$–$C_8$ alkyliminobis-propylamines such as octylimino-bis-propylamine, methyl-imino-bis-propylamine, and imino-bis-propylamine.

The polyamine can be mixed with the particulate carrier in a vessel provided with a gas inlet tube and an agitator. Carbon dioxide gas is fed into the vessel containing the polyamine adsorbed on the carrier at a rate at which the gas can be adsorbed. Conveniently, the carbon dioxide is added to the polyamine adsorbed on the carrier at a rate of about 1–7 liters of carbon dioxide (at SPT)/ hour/mole polyamine. Although only one mole of carbon dioxide per mole of polyamine is consumed during the reaction, it is preferred to introduce an excess of carbon dioxide to ensure complete utilization of the amine in a reasonable period of time.

The present invention can be carried out under either batch or continuous conditions. In a batch process a predetermined amount of polyamine is adsorbed on a predetermined amount of carrier and carbon dioxide is added until all the polyamine has been converted to polyamine carbamate. The amount of carrier used in the process can vary widely, but generally the amount used is between about 10–50% of the total weight of the polyamine. Preferably, a continuous process is employed, in which case carrier, polyamine, and carbon dioxide are all fed to the reaction vessel continuously and simultaneously. Under such conditions the amount of carrier is continuously changing. However, at the start of the operations the ratio of carrier to polyamine is within the same range as employed with the batch technique.

The reaction is carried out in a closed vessel usually at atmospheric pressure, although higher or lower pressures can be used if desired. No solvent for the reactants, i.e., polyamine and carbon dioxide, or the resulting polyamine carbamate, is used in the process. The reaction is exothermic and, therefore, the reaction mixture is cooled to avoid dissociation of the resulting polyamine carbamate. Since the dissociation of the polyamine carbamates suitable for vulcanization occurs at temperatures in excess of about 100° C, the reaction mixture should be maintained at temperatures less than the dissociation temperature of the carbamate. Temperatures less than about 90° C are suitable but the preferred temperature range at which the reaction mixture is maintained is between about 25°–40° C. Temperatures much lower than about 10° C are not practical operating temperatures. Since the particle size of the carbamate-carrier mixture is quite small it is often desirable to conduct the reaction in the presence of an anti-dusting agent for the carbamate. Such anti-dusting agents are well known and include hydrocarbon oils and fibrillated poly(tetrafluoroethylene).

The reaction of the carbon dioxide with the polyamine adsorbed on the particulate carrier results in a polyamine carbamate-carrier mixture in free-flowing form due to the conditions of the reaction.

The polyamine carbamate is added in conventional amounts, e.g., 1–2%, to the polymer that is to be cured. The polymer is cured by conventional procedures, e.g., heating for 5–60 minutes at 100°–205° C.

For a further understanding of the invention, the following examples are presented as illustrative of the process, and they are not to be considered as limiting the the underlying principles of the invention.

EXAMPLES

EXAMPLE 1

To a 1-liter resin flask equipped with a stainless steel stirrer, a metal dial thermometer, a gas inlet tube and an addition funnel were added 118 g. precipitated silica (sold as "Hi-Sil" 215 by PPG Industries). Seventy-four grams 1,2-diaminopropane were added over a period of 45 min. while rapidly stirring. When the addition was completed, a line leading to a bubbler containing mineral oil was attached to the addition funnel. The stirred mixture was cooled by an ice-water bath while carbon dioxide was fed from a cylinder at the rate the gas could be adsorbed, as indicated by the bubbler. The temperature was kept below 30° C. After ten minutes of carbon dioxide addition, 59 g. of a hydrocarbon oil anti-dusting agent (sold as Circo Light Process Oil by Sun Oil Company) were added dropwise over a period of two and one-half hours along with the carbon dioxide. Stirring was continued for an hour under a carbon dioxide atmosphere after the oil addition was completed. The resulting 1,2-diaminopropane carbamate-carrier mixture was in finely divided powder form which was relatively non-dusting and weighed 283.5 g. (96% of theoretical yield). The carbamate content of the powder was 38.5% by weight.

EXAMPLE 2

Twenty-five grams fumed silica (sold as "Cab-O-Sil" M5 by Cabot Corp.), 50 g. methylimino-bis-propylamine and 500 ml. 1,1,2-trichloro-1,2,2-trifluoroethane were placed into the flask of a rotary evaporator. Removal of the solvent gave a material containing soft granules of about 2 mm. diameter. The material was placed in a mortar and a further 25 g. of the silica was added. Upon mixing, the material became a free-flowing powder. The powder was placed in a 1-liter resin flask equipped with a stainless steel stirrer, a metal dial thermometer, a gas inlet tube and an exit line leading to a bubbler containing mineral oil. The powder was stirred and cooled by an ice-water bath while carbon dioxide was fed from a cylinder at the rate the gas could be adsorbed, as indicated by the bubbler. The temperature was kept below 30° C. After two hours of carbon dioxide addition, no further absorption of gas was evident. The fine dusty carbamate-carrier mixture weighed 116.2 g, indicating 100% conversion of the diamine to carbamate.

EXAMPLES 3–6

The procedure described in Example 1 was repeated using the carriers, polyamines and anti-dusting agents listed in Table I. Yields of the carbamate-carrier compositions are indicated as % of theory.

TABLE I

| Example | Carrier | Polyamine | Anti-Dusting Agent | Carbamate-Carrier Mixture Yield |
|---|---|---|---|---|
| 3 | Silica ("Hi-Sil" 215) (80 g.) | 1,6-Diaminohexane (58 g.) | Circo Light Process Oil (40 g.) | 97.8% 1,6-diaminohexane carbamate-carrier |
| 4 | MgCO$_3$ (50 g.) | 1,6-Diaminohexane (20 g.) | Circo Light Process Oil (10 g.) | 95% 1,6-diaminohexane carbamate-carrier |
| 5 | Silica ("Hi-Sil" 215) (100 g.) | 4,4'-Methylene bis (cyclohexylamine) (100 g.) | Hydrocarbon Oil[a] (55 g.) | 4,4' Methylene bis (cyclohexylamine) carbamate-carrier |
| 6 | Silica ("Hi-Sil" 215) (50 g.) | 1,2-Diaminopropane (50 g.) | Fibrillated Poly (tetra-fluoroethylene)[b] (1 g.) | 1,2-Diaminopropane carbamate-carrier |

[a]NPA color 4.0, flash pont 330° F, viscosity 210 at 100° F
[b]Sold as "Teflon" K by E. I. du Pont de Nemours & Co., Inc.

EXAMPLE 7

Sixty grams fumed silica (sold as "Cab-O-Sil" MS-7 by Cabot Corp.) were agitated in a 1-liter flat bottom reaction kettle under a carbon dioxide atmosphere. The kettle was fitted with a stirrer, a gas inlet and an inlet from a pump. 1,2-Diaminopropane and carbon dioxide were simultaneously added via the pump and gas inlets over a period of 7.5 hrs. while the temperature was kept at 25°–30° C. At the end of this time 211 g. of 1,2-diaminopropane carbamate had been formed.

EXAMPLE 8

A. The procedure of Example 7 was repeated except that a similarly equipped ribbon blender was used and 3.40 kg. of 1,2-diaminopropane carbamate were used as the carrier, instead of the fumed silica. 1,2-Diaminopropane (12.23 kg.) and excess carbon dioxide were added simultaneously for 11 hrs. while the temperature was kept at 40°–50° C. At this time, there was recovered a total of 22.42 kg. of 1,2-diaminopropane carbamate of 98.53% purity.

B. The general procedure of A was repeated except that 2.26 kg. of the 1,2-diaminopropane carbamate produced in A were used as the carrier. The addition of 7.70 kg. 1,2-diaminopropane and excess carbon dioxide over a period of 12 hrs. yielded 14.24 kg. of 1,2-diaminopropane carbamate of 98.20% purity.

EXAMPLES 9–11

The general procedure described in Example 7 was repeated using the carriers, polyamines, and conditions shown in Table II.

TABLE II

| Example | Carrier | Diamine | Addition Time | Yield Carbamate[a] Purity |
|---|---|---|---|---|
| 9 | Calcium Carnonate[b] (100 g.) | Methylene bis-(4-cyclohexylamine) | 8 hrs. | 226 g. Methylene bis-(4-cyclohexylamine) carbamate |
| 10 | Carbamate[c] (84.8 g.) | Methylene bis-(4-cyclohexylamine) | 5.5 hrs. | 301 g. (96.94%) Methylene bis-(4-cyclohexylamine) carbamate |
| 11 | Carbamate[d] (100 g.) | 1,2-Diaminopropane | 26 hrs. | 847 g. (97.88%) 1,2-Propylenediamine carbamate |

[a] Does not include carrier
[b] Sold as "Omylite" 90 by Tluess-Stafer, North American
[c] Methylene-bis(4-cyclohexylamine) carbamate
[d] 1,2-Propylenediamine carbamate

I claim:

1. In a process for preparing a polyamine carbamate which comprises reacting an aliphatic or cycloaliphatic polyamine having 2–14 carbon atoms and two primary amino groups with gaseous carbon dioxide, the improvement which comprises mixing said polyamine and a particulate carrier capable of adsorbing the polyamine and selected from the group consisting of an inorganic material inert to the reaction of polyamine with carbon dioxide or a polyamine carbamate that is the same as the carbamate being produced and reacting the polyamine on the carrier with at least 1 mole carbon dioxide per mole polyamine in the absence of solvent for the reactants at a temperature less than about 90° C to obtain the free-flowing, corresponding polyamine carbamate-carrier mixture.

2. A process of claim 1 wherein the carrier is a polyamine carbamate that is the same as the carbamate being produced.

3. A process of claim 1 wherein the carrier is an inorganic material inert to the reaction of polyamine with carbon dioxide.

4. A process of claim 3 wherein the carrier is silica.

5. A process of claim 3 wherein the carrier is magnesium carbonate.

6. A process of claim 3 wherein the carrier is calcium carbonate.

7. A process of claim 2 wherein the carrier is 1,2-diaminopropane carbamate.

8. A process of claim 2 wherein the carrier is methylenebis(4-cyclohexylamine) carbamate.

9. A process of claim 1 wherein the polyamine is 1,2-diaminopropane.

10. A process of claim 1 wherein the polyamine is 1,6-diaminohexane.

11. A process of claim 1 wherein the polyamine is 4,4-methylenebis(4-cyclohexylamine).

12. A process of claim 1 wherein the polyamine is methylimino-bis-propylamine.

13. A process of claim 1 wherein the reaction is carried out in the presence of an anti-dusting agent for the resulting carbamate that is a hydrocarbon oil or fibrillated poly(tetrafluoroethylene).

* * * * *